US011288980B2

(12) United States Patent
Larsen et al.

(10) Patent No.: US 11,288,980 B2
(45) Date of Patent: Mar. 29, 2022

(54) ELECTRIFIED ANATOMICAL MODEL

(71) Applicant: Boston Scientific Scimed Inc., Maple Grove, MN (US)

(72) Inventors: Steven R. Larsen, Lino Lakes, MN (US); Daniel H. VanCamp, Elk River, MN (US); Kai Wang, Plymouth, MN (US); Steve L. Erickson, Anoka, MN (US); Ronson L. Yong, Shoreview, MN (US); Buffi Jo Langley, Hanover, MN (US); David J. Holtan, Eden Prairie, MN (US); Joseph W. Tushar, Hanover, MN (US); Robbie Halvorson, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 746 days.

(21) Appl. No.: 15/928,365

(22) Filed: Mar. 22, 2018

(65) Prior Publication Data

US 2018/0277021 A1  Sep. 27, 2018

Related U.S. Application Data

(60) Provisional application No. 62/475,157, filed on Mar. 22, 2017.

(51) Int. Cl.
*G09B 23/30* (2006.01)
*G09B 23/28* (2006.01)
(Continued)

(52) U.S. Cl.
CPC .............. *G09B 23/30* (2013.01); *A61B 5/319* (2021.01); *B29C 64/10* (2017.08);
(Continued)

(58) Field of Classification Search
CPC .......... G09B 23/30; G09B 9/00; G09B 23/28; B33Y 10/00; B33Y 80/00; B29C 64/10;
(Continued)

(56) References Cited

U.S. PATENT DOCUMENTS 5,041,973 A * 8/1991 Lebron .................... 364/413.05
8,834,172 B2 * 9/2014 Rubinstein ............. G09B 23/30
                                                              434/267
(Continued)

FOREIGN PATENT DOCUMENTS

CN      103026519 A     4/2013
CN      103245708 A     8/2013
(Continued)

OTHER PUBLICATIONS

Connolly, A. A Virtual Heart Model for Formal and Functional Medical Device Verification. 17 pages [available at least as early as Oct. 18, 2016].
(Continued)

*Primary Examiner* — Robert J Utama
(74) *Attorney, Agent, or Firm* — Faegre Drinker Biddle & Reath LLP

(57) ABSTRACT

An anatomical model simulator system includes an anatomical model assembly. The anatomical model assembly includes an anatomical model shell having a plurality of apertures defined therein; and a plurality of electrodes. Each electrode of the plurality of electrodes is disposed within one of the plurality of apertures, and each electrode includes at least one of carbon black and silver epoxy. The anatomical model simulator system also includes a model control system. The model control system includes a power supply configured to deliver electrical energy to the plurality of electrodes; and a controller configured to control the delivery of the electrical energy to the plurality of electrodes.

12 Claims, 7 Drawing Sheets

(51) Int. Cl.
*G09B 9/00* (2006.01)
*B29C 64/10* (2017.01)
*B33Y 80/00* (2015.01)
*B29C 65/48* (2006.01)
*B33Y 10/00* (2015.01)
*A61B 5/319* (2021.01)
*A61B 5/283* (2021.01)

(52) U.S. Cl.
CPC .......... *B29C 65/4885* (2013.01); *B33Y 10/00* (2014.12); *B33Y 80/00* (2014.12); *G09B 9/00* (2013.01); *A61B 5/283* (2021.01); *G09B 23/28* (2013.01)

(58) Field of Classification Search
CPC .. B29C 65/4885; A61B 5/04021; A61B 5/042
USPC .......................................................... 434/272
See application file for complete search history.

(56) References Cited

U.S. PATENT DOCUMENTS

| | | | | |
|---|---|---|---|---|
| 2005/0130107 | A1* | 6/2005 | Ellingson | 434/272 |
| 2006/0004273 | A1 | 1/2006 | Lobodzinski | |
| 2008/0161681 | A1* | 7/2008 | Hauck | A61B 34/20 |
| | | | | 600/424 |
| 2010/0198040 | A1 | 8/2010 | Friedman et al. | |
| 2012/0043858 | A1* | 2/2012 | Mahapatra | F03G 7/005 |
| | | | | 310/339 |
| 2014/0277678 | A1* | 9/2014 | Vesto | B29C 64/386 |
| | | | | 700/119 |
| 2014/0303470 | A1* | 10/2014 | Tsukada | D06P 1/38 |
| | | | | 600/377 |
| 2015/0064675 | A1* | 3/2015 | Eichhorn | A61B 34/76 |
| | | | | 434/262 |
| 2015/0250934 | A1* | 9/2015 | Min | B33Y 80/00 |
| | | | | 623/3.11 |
| 2015/0313491 | A1* | 11/2015 | Edwards | A61B 5/0422 |
| | | | | 600/374 |
| 2016/0374615 | A1 | 12/2016 | Tsukada et al. | |
| 2017/0143414 | A1* | 5/2017 | Sliwa | A61B 18/1492 |
| 2017/0185740 | A1* | 6/2017 | Seegerer | A61B 5/0452 |
| 2018/0315347 | A1* | 11/2018 | Zhu | G09B 23/32 |

FOREIGN PATENT DOCUMENTS

| | | |
|---|---|---|
| CN | 103489360 A | 1/2014 |
| WO | 2010088325 A2 | 8/2010 |
| WO | 2016183179 A1 | 11/2016 |

OTHER PUBLICATIONS

International Search Report and Written Opinion issued in PCT/US2018/023711, dated Jun. 19, 2018, 11 pages.
Kim, D.-H. et al. Flexible and Stretchable Electronics for Biointegrated Devices. Annu. Rev. Biomed. Eng. 2012, 14:113-128.
Xia, L. et al. Beating Heart Modeling and Simulation. Computers in Cardiology, 31:137-140, 2004.

* cited by examiner

ELECTRIFIED ANATOMICAL MODEL

CROSS-REFERENCE TO RELATED APPLICATION

This application claims priority to Provisional Application No. 62/475,157, filed Mar. 22, 2017, which is herein incorporated by reference in its entirety.

TECHNICAL FIELD

The present disclosure relates to medical devices and methods for simulating an anatomical structure of the body. More specifically, the disclosure relates to devices and methods for providing a simulation environment for use with an electroanatomical mapping system.

BACKGROUND

In electrophysiology, mapping is often used to identify the earliest site of atrial or ventricular activation or evidence of a slow zone of conduction. To test, or demonstrate, an electroanatomical mapping system, an animal generally is sacrificed. An anatomical model system may facilitate minimizing the harm to animals and enhancing convenience in testing and demonstrating mapping systems.

SUMMARY

Embodiments include an anatomical model assembly configured to provide a simulated environment for a mapping system. In embodiments, the anatomical model assembly utilizes electrodes that generate the simulated physiological electrical signals. The electrodes may be designed to achieve relative capacitances that facilitate detection of the electrical signals by the mapping system.

In an Example 1, an electrode assembly for use in an anatomical model assembly, the electrode assembly comprising: an electrode configured to be at least partially disposed within an aperture defined in an anatomical model shell, the electrode comprising a capacitive material, the capacitive material comprising a mixture of carbon black and silver epoxy; and a header coupled to the electrode.

In an Example 2, the electrode assembly of Example 1, the mixture comprising approximately 50% carbon black and approximately 50% silver epoxy.

In an Example 3, the electrode assembly of either of Examples 1 or 2, the header configured to receive an end of a wire, wherein the end of the wire is coupled to the electrode.

In an Example 4, the electrode assembly of any of Examples 1-3, wherein the electrode has an approximately cylindrical shape.

In an Example 5, the electrode assembly of Example 4, wherein the electrode comprises a diameter of approximately two millimeters.

In an Example 6, an anatomical model simulator system, comprising: an anatomical model assembly, comprising: an anatomical model shell having a plurality of apertures defined therein; and a plurality of electrodes, wherein each electrode of the plurality of electrodes is disposed within one of the plurality of apertures, and wherein each electrode comprises at least one of carbon black and silver epoxy; and a model control system, comprising: a power supply configured to deliver electrical energy to the plurality of electrodes; and a controller configured to control the delivery of the electrical energy to the plurality of electrodes.

In an Example 7, the anatomical model simulator system of Example 6, the anatomical shell comprising an inside surface, wherein an end surface of each electrode of the plurality of electrodes is recessed with respect to the inside surface of the anatomical shell.

In an Example 8, the anatomical model stimulator system of either of Examples 6 or 7, wherein the anatomical shell is formed from a three-dimensionally printed polymer.

In an Example 9, the anatomical model stimulator system of any of Examples 6-8, the plurality of electrodes comprising a plurality of pairs of electrodes, each of the plurality of pairs of electrodes comprising a positive electrode and a negative electrode.

In an Example 10, the anatomical model stimulator system of Example 9, wherein each of the plurality of pairs of electrodes is configured to generate an electric field having a magnitude that can be sensed by a mapping probe.

In an Example 11, the anatomical model stimulator system of Example 10, wherein the electrode is configured to be driven with approximately 0.1 volts.

In an Example 12, the anatomical model stimulator system of any of Examples 6-11, the controller comprising: a switch circuit configured to selectively activate each of the plurality of electrodes; a memory comprising a program component, the program component comprising computer-executable instructions; and a processor configured to access the program component via the memory and to executed the computer-executable instructions, wherein the computer-executable instructions are configured to cause the processor to control the power supply.

In an Example 13, the anatomical model stimulator system of Example 12, wherein the controller is configured to cause the power supply to deliver the electrical energy according to an arrhythmia pattern to cause the plurality of electrodes to simulate a propagating cardiac electrical signal corresponding to an arrhythmia.

In an Example 14, the anatomical model stimulator system of Example 12, wherein the controller is configured to prevent electrical energy from being delivered to one or more pairs of electrodes to simulate scar tissue.

In an Example 15, a method of producing an anatomical model simulator system, the method comprising: forming a first anatomical model shell piece, the first anatomical model shell piece comprising a first plurality of apertures defined therein; forming a second anatomical model shell piece, the second anatomical model shell piece comprising a second plurality of apertures defined therein; creating a mixture of carbon black and silver epoxy; positioning an end of a wire within an aperture of the first plurality of apertures; securing the end of the wire in position using an epoxy; filling the aperture with the mixture of carbon black and silver epoxy; and coupling the first and second anatomical model shell pieces to form an anatomical model shell.

In an Example 16, an electrode assembly for use in an anatomical model assembly, the electrode assembly comprising: an electrode configured to be at least partially disposed within an aperture defined in an anatomical model shell, the electrode comprising a capacitive material, the capacitive material comprising a mixture of carbon black and silver epoxy; and a header coupled to the electrode.

In an Example 17, the electrode assembly of Example 16, the mixture comprising approximately 50% carbon black and approximately 50% silver epoxy.

In an Example 18, the electrode assembly of Example 16, the header configured to receive an end of a wire, wherein the end of the wire is coupled to the electrode.

In an Example 19, the electrode assembly of Example 16, wherein the electrode has an approximately cylindrical shape.

In an Example 20, the electrode assembly of Example 19, wherein the electrode comprises a diameter of approximately two millimeters.

In an Example 21, an anatomical model simulator system, comprising: an anatomical model assembly, comprising: an anatomical model shell having a plurality of apertures defined therein; and a plurality of electrodes, wherein each electrode of the plurality of electrodes is disposed within one of the plurality of apertures, and wherein each electrode comprises at least one of carbon black and silver epoxy; and a model control system, comprising: a power supply configured to deliver electrical energy to the plurality of electrodes; and a controller configured to control the delivery of the electrical energy to the plurality of electrodes.

In an Example 22, the anatomical model simulator system of Example 21, the anatomical shell comprising an inside surface, wherein an end surface of each electrode of the plurality of electrodes is recessed with respect to the inside surface of the anatomical shell.

In an Example 23, the anatomical model stimulator system of Example 21, wherein the anatomical shell is formed from a three-dimensionally printed polymer.

In an Example 24, the anatomical model stimulator system of Example 21, the plurality of electrodes comprising a plurality of pairs of electrodes, each of the plurality of pairs of electrodes comprising a positive electrode and a negative electrode.

In an Example 25, the anatomical model stimulator system of Example 24, wherein each of the plurality of pairs of electrodes is configured to generate an electric field having a magnitude that can be sensed by a mapping probe.

In an Example 26, the anatomical model stimulator system of Example 25, wherein the electrode is configured to be driven with approximately 0.1 volts.

In an Example 27, the anatomical model stimulator system of Example 21, the controller comprising: a switch circuit configured to selectively activate each of the plurality of electrodes; a memory comprising a program component, the program component comprising computer-executable instructions; and a processor configured to access the program component via the memory and to executed the computer-executable instructions, wherein the computer-executable instructions are configured to cause the processor to control the power supply.

In an Example 28, the anatomical model stimulator system of Example 27, wherein the controller is configured to cause the power supply to deliver the electrical energy according to an arrhythmia pattern to cause the plurality of electrodes to simulate a propagating cardiac electrical signal corresponding to an arrhythmia.

In an Example 29, the anatomical model stimulator system of Example 28, wherein the controller is configured to prevent electrical energy from being delivered to one or more pairs of electrodes to simulate scar tissue.

In an Example 30, the anatomical model stimulator system of Example 21, each of the plurality of electrodes comprising a mixture comprising approximately 50% carbon black and approximately 50% silver epoxy.

In an Example 31, the anatomical model stimulator system of Example 30, each of the plurality of electrodes having an approximately cylindrical shape.

In an Example 32, the anatomical model stimulator system of Example 30, wherein each of the plurality of electrodes comprises a diameter of approximately two millimeters.

In an Example 33, a method of producing an anatomical model simulator system, the method comprising: forming a first anatomical model shell piece, the first anatomical model shell piece comprising a first plurality of apertures defined therein; forming a second anatomical model shell piece, the second anatomical model shell piece comprising a second plurality of apertures defined therein; creating a mixture of carbon black and silver epoxy; positioning an end of a wire within an aperture of the first plurality of apertures securing the end of the wire in position using an epoxy; filling the aperture with the mixture of carbon black and silver epoxy; and coupling the first and second anatomical model shell pieces to form an anatomical model shell.

In an Example 34, the method of Example 33, the mixture comprising approximately 50% carbon black and approximately 50% silver epoxy.

In an Example 35, the method of Example 32, wherein the steps of forming the first and second anatomical model shell pieces comprise three-dimensionally printing the first and second anatomical model shell pieces.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1A:
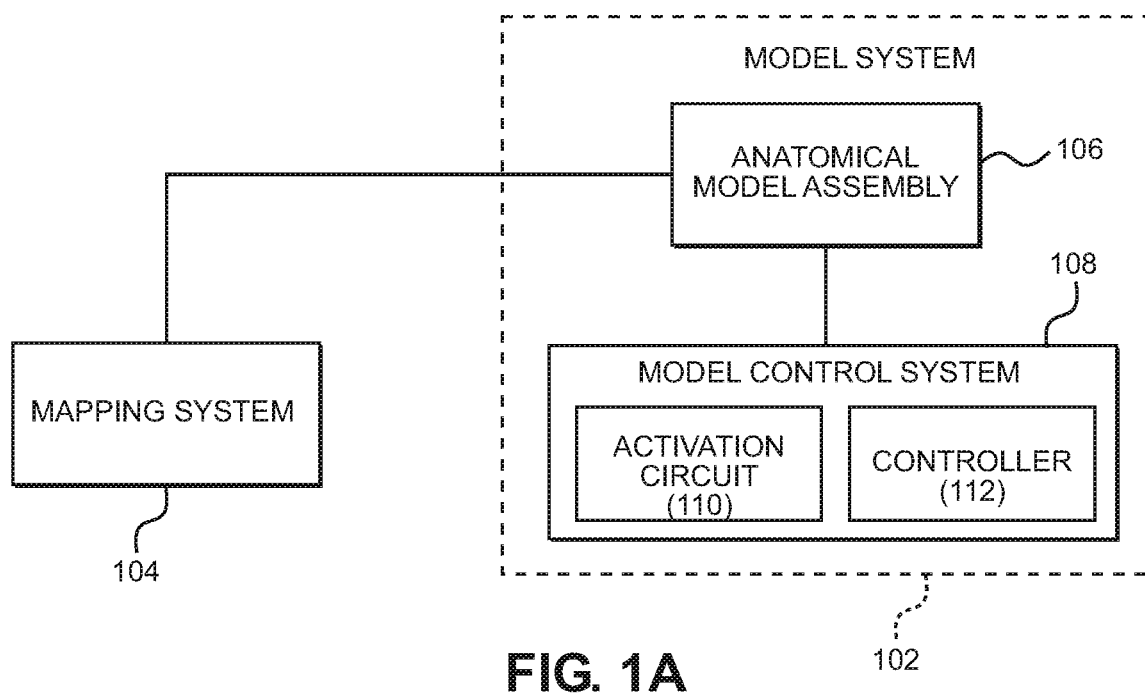
FIGS. 1A and 1B are block diagrams of an anatomical model simulator system configured to provide a simulated mapping environment for use with a mapping system, in accordance with embodiments of the subject matter disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

As used herein, the term "based on" is not meant to be restrictive, but rather indicates that a determination, identification, prediction, calculation, and/or the like, is performed by using at least the term following "based on" as an input. For example, if an algorithm step is described as "predicting an outcome based on a first piece of information," that predicting step may additionally include predicting the outcome based on a second piece of information, and/or any other additional pieces of information.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Figure 1B:
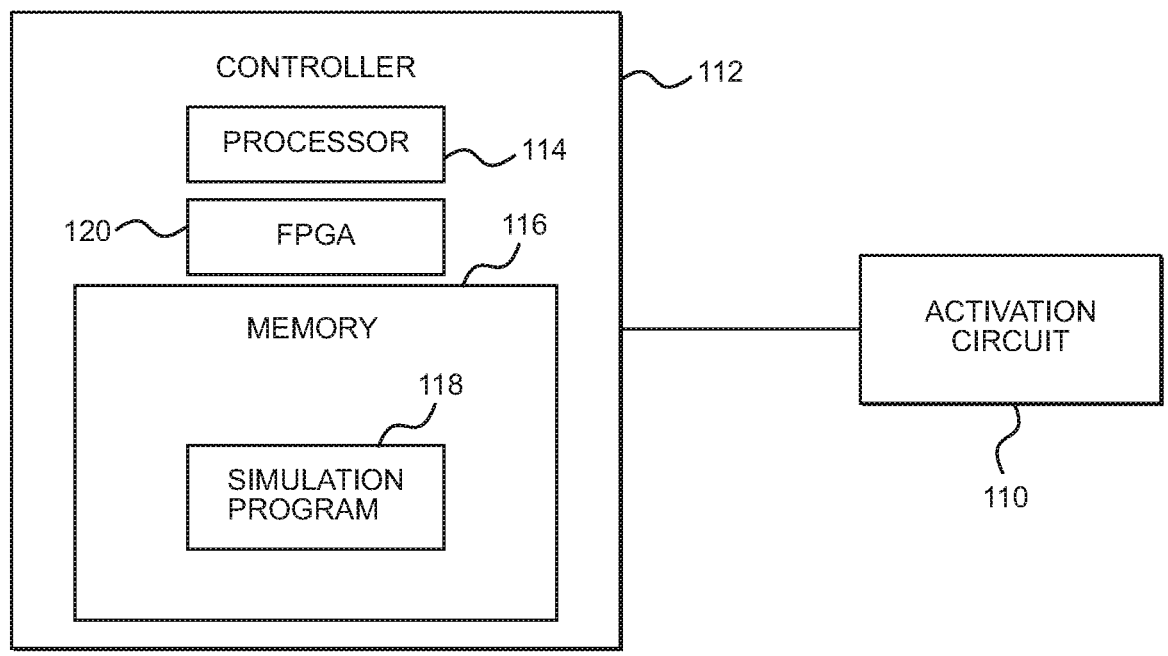

FIGS. 1A and 1B are block diagrams of an anatomical model simulator system 102 configured to provide a simulated mapping environment for use with a mapping system 104, in accordance with embodiments of the subject matter disclosed herein. The system 102 includes an anatomical model assembly 106 that is controlled by a model control system 108. According to embodiments, the anatomical model simulator system 102 may be used to test a mapping system (or an aspect thereof such as, e.g., a mapping probe), to demonstrate a mapping system (or an aspect thereof), to demonstrate mapping techniques, to demonstrate physiological phenomena, and/or the like. For example, in embodiments, the anatomical model simulator system 102 may include a testing environment for a mapping probe such as, for example, a mapping catheter, an ablation catheter, and/or any other device configured to sense physiological electrical signals within a subject's anatomy. The subject may be, for example, a human patient or an animal. The mapping system 104 may be any device and/or system configured to perform electro-anatomical mapping of an anatomical structure such as, for example, a heart, an intestine, a colon, and/or the like.

The anatomical model assembly 106 is a physical model configured to represent an anatomical structure such as, for example, a heart, an intestine, a colon, and/or the like. For purposes of clarity of description, embodiments of the anatomical model assembly 106 are described herein (e.g., below with reference to FIGS. 2A-2D) with respect to a model configured to represent a heart, or a portion of a heart. However, this is not intended to limit the scope of the subject matter disclosed herein, but rather is intended to be only a representative example. As such, it is contemplated that the anatomical model assembly 106 may be configured to represent any anatomical structure through which physiological electrical signals pass that may be capable of being sensed using a mapping system 104 or aspect thereof.

The model control system 108 includes an activation circuit 110 configured to deliver electrical energy to the electrodes and a controller 112 configured to control the delivery of the electrical energy to the electrodes (e.g., by controlling the activation circuit 110). In embodiments, the activation circuit 110 may include one or more switch matrices, and/or the like. The activation circuit 110 may include any number of different types of electrical components and may, for example, include electrical circuits, digital output modules, analog output modules, and/or the like. For example, the activation circuit 110 may be, or include, multiple analog remote output modules such as those available from National Instruments Corporation of Austin, Tex. The analog output modules may be configured to function in a similar manner as a digital-to-analog converter (DAC). In embodiments, for example, the controller 112 may be, or include components of the CompactRio platform, available from National Instruments Corporation of Austin, Tex.

As shown in FIG. 1B, the controller 112 includes a processor 114 configured to executed computer-executable instructions 118 stored in a memory 116 to control the activation circuit 110. The controller 112 also may include a field-programmable gate array (FPGA) 120 configured to facilitate synchronously timed and simultaneous outputs to the activation circuit (e.g., analog output modules) 110. For example, in embodiments, to simulate an activation cascade, multiple electrodes, and/or pairs of electrodes, are to be activated approximately simultaneously, which may require parallel process operations to be performed by the controller 112. The FPGA may be configured to facilitate these parallel process operations.

The activation circuit 110 may be configured to selectively activate one or more of the electrodes. According to various embodiments of the disclosed subject matter, any number of the components depicted in FIG. 1 (e.g., the model system 102, the mapping system 104, the model control system 108, and/or the controller 112) may be implemented on one or more computing devices. Accordance with embodiments of the disclosure, a computing device may include any type of computing device suitable for implementing aspects of embodiments of the disclosed subject matter. Examples of computing devices include specialized computing devices or general-purpose computing devices such "workstations," "servers," "laptops," "desktops," "tablet computers," "programmers," "hand-held devices," "general-purpose graphics processing units (GPGPUs)," and the like, all of which are contemplated within the scope of FIGS. 1A and 1B, with reference to various components of the system 102.

In embodiments, a computing device includes a bus that, directly and/or indirectly, couples devices such as, for example, the processor 114, the memory 116, an input/output (I/O) port, an I/O component (e.g., a display device, an auditory device, the activation circuit 110, a mapping probe, etc.). Any number of additional components, different components, and/or combinations of components may also be included in the computing device. The I/O component may include a presentation component configured to present information to a user such as, for example, a display device, a speaker, a printing device, the activation circuit 110, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, a mapping probe, and/or the like.

The bus represents what may be one or more busses (such as, for example, an address bus, data bus, or combination thereof). Similarly, in embodiments, the computing device may include a number of processors 114, a number of memory components 116, a number of I/O ports, a number of I/O components, and/or a number of power supplies. Additionally any number of these components, or combinations thereof, may be distributed and/or duplicated across a number of computing devices.

In embodiments, the memory 116 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 116 stores computer-executable instructions for causing the processor 114 to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors 114 associated with the computing device. As shown in FIG. 1B, a program component may include a simulation program 118 that may be configured to cause the processor 114, upon being executed, to control the activation circuit 110 to deliver electrical energy to a set of electrodes according to a pattern that simulates a specified activation propagation, arrhythmia, and/or the like. Program components may be programmed using any number of different programming environments, including various languages, development kits, frameworks, and/or the like. Some or all of the functionality contemplated herein may also, or alternatively, be implemented in hardware and/or firmware.

According to embodiments, the controller 112 is configured to cause the activation circuit 110 to deliver the electrical energy according to an activation propagation pattern, which may be predetermined or dynamically determined. For example, in embodiments, each pair of electrodes may correspond to a switchable channel in the activation circuit and the controller 112 may be configured to implement programmable delays to facilitate activating sequential pairs of electrodes to simulate a propagating activation front. For example, the activation circuit may include a number of outputs, each having a reference designator, and each corresponding to an electrode or electrode pair. The controller 112 may, as a result of executing a simulation program 118, use the reference designators to specify which electrode or electrode pair to activate at which time.

In embodiments, the memory 116 may include a number of simulation programs 118, each designed to facilitate a different type of simulation. For example, the simulation programs 118 may be configured to facilitate simulation of arrhythmic conditions such as fibrillation, ischemic defects, bradycardia, tachycardia, automaticity, and/or the like. In embodiments, programmable delays may be implemented by the controller 112 to prevent electrical energy from being delivered to one or more pairs of electrodes to simulate scar tissue. In other embodiments, the electrodes may be hardwired in a particular pattern, and the activation circuit 110 may include a time delay circuit (e.g., a shift register) configured to facilitate causing the electrodes to activate in a linear cascade, thereby simulating, e.g., a sinus rhythm. Any combination of static and dynamic simulation configurations may be implemented in accordance with embodiments of the disclosure. In embodiments, the controller 112 also may be configured to generate a simulated electrocardiogram (ECG) signal to serve as a stable time reference for the mapping system 104. In embodiments, the controller 112 may output an ECG signal via electrodes so that the mapping system 104 may sense the ECG signal, while, in other embodiments, the controller 112 may be configured to communicate the ECG signal to the mapping system 104. According to embodiments, the activation circuit 110 may be configured to generate the ECG signal.

The illustrative anatomical model simulator system 102 shown in FIGS. 1A and 1B is not intended to suggest any limitation as to the scope of use or functionality of embodiments of the present disclosure. Neither should the illustrative anatomical model simulator system 102 be interpreted as having any dependency nor requirement related to any single component or combination of components illustrated therein. Additionally, various components depicted in FIGS. 1A and 1B may be, in embodiments, integrated with various ones of the other components depicted therein (and/or components not illustrated), all of which are considered to be within the ambit of the present disclosure.

Figure 2A:
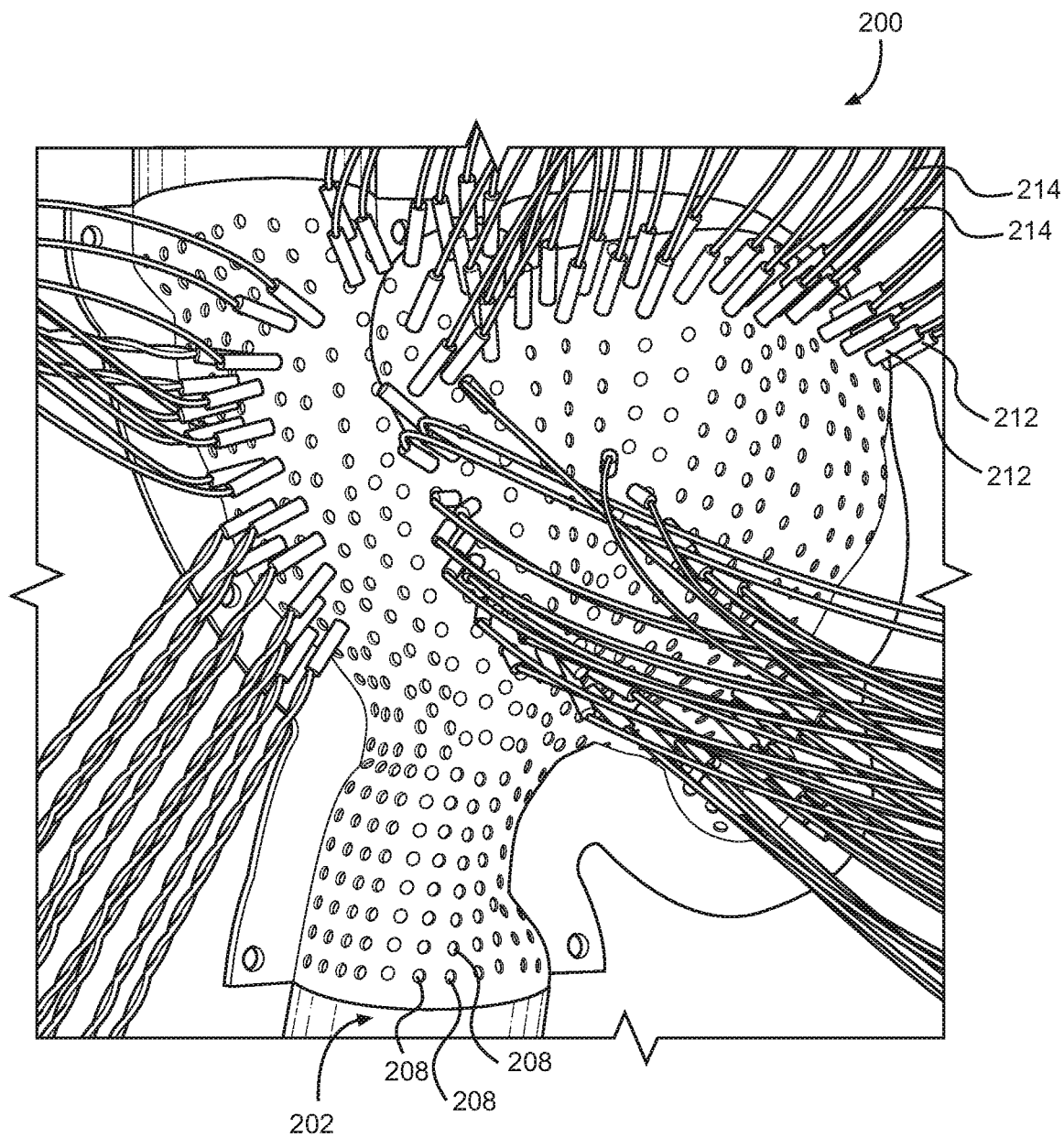
FIGS. 2A-2C depict various perspective views of an anatomical model assembly that is configured to represent a human atrium, in accordance with embodiments of the disclosed subject matter.
Figure 2B:
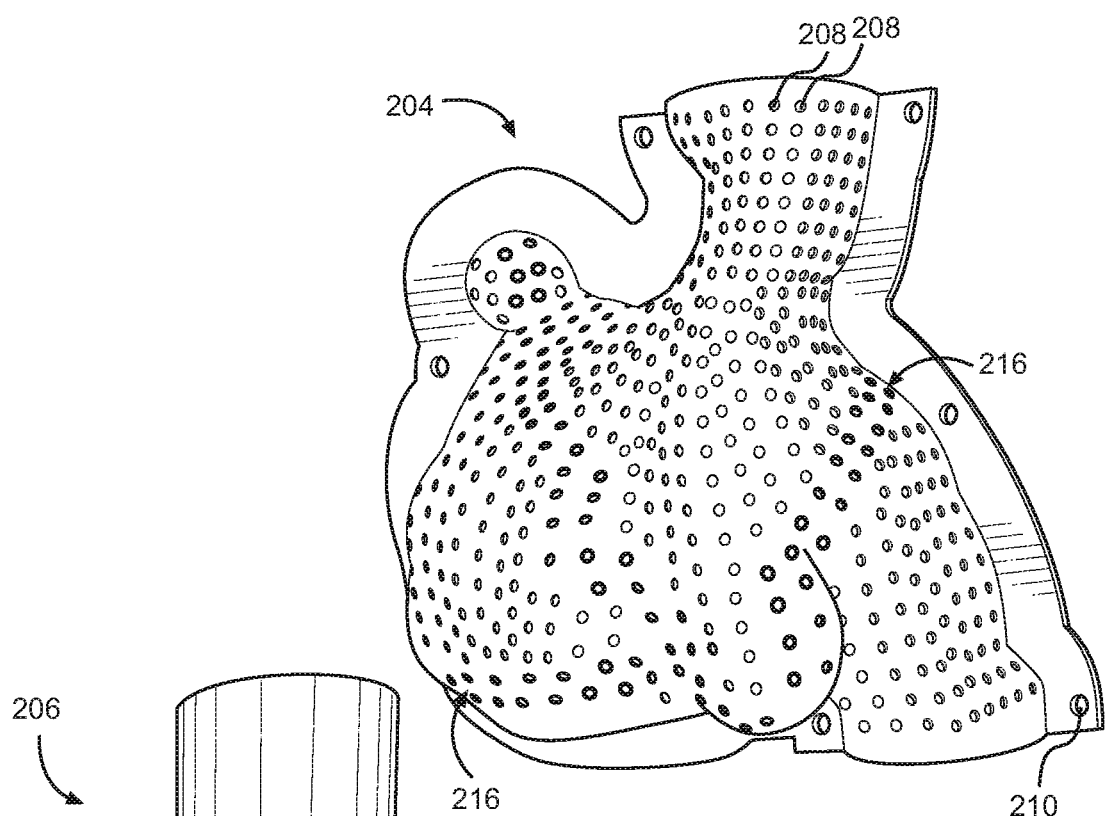
Figure 2C:
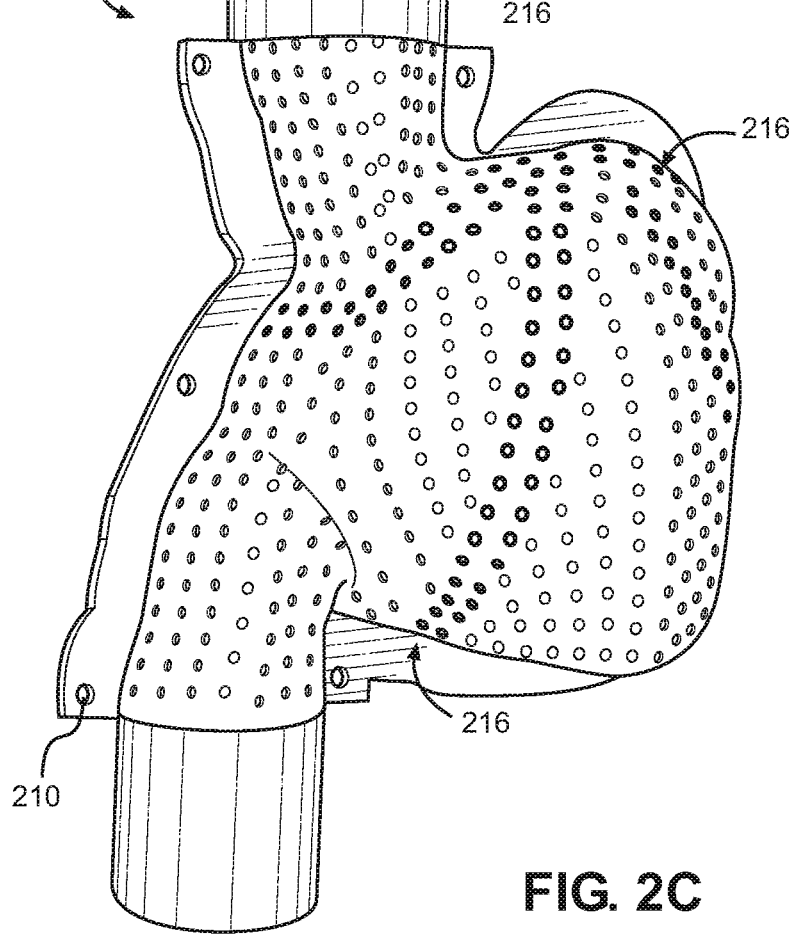

FIGS. 2A-2C depict various perspective views of an anatomical model assembly 200 that is configured to represent a human atrium, in accordance with embodiments of the disclosed subject matter. In embodiments, the anatomical model assembly may be, be similar to, include similar features as, include, or be included within the anatomical model assembly 106 described above with reference to FIG. 1A. The anatomical model assembly 200 includes an anatomical model shell 202 formed using a first anatomical model shell piece 204 and a second anatomical model shell piece 206, each of the first and second shell pieces 204 and 206 having apertures 208 defined therein. In embodiments, the first and second anatomical model shell pieces 204 and 206 may be formed from any material that will hold a particular shape and that will not interfere with the functionality of the model assembly 200 (e.g., by causing interference with electrical fields, etc.). For example, the anatomical model shell pieces 204 and 206 may be formed from a solid polymer. In embodiments, the anatomical model shell pieces may be formed from any soft or hard, solid insulator such as, for example, silicone, polyethylene, PTFE, and/or the like.

The anatomical model shell pieces 204 and 206 may be formed using any number of different types of manufacturing processes including, for example, three-dimensionally printing ("3D printing"), casting, machining, injection molding, and/or the like. In embodiments, the anatomical model shell pieces 204 and 206 may be formed with one or more of the apertures defined therein (e.g., by 3D printing a polymer piece having a shape that includes the apertures). In embodiments, one or more of the apertures may be formed after the anatomical model shell pieces 204 and 206 are created such as, for example, by machining the anatomical model shell pieces 204 and 206. Each of the anatomical model shell pieces 204 and 206 may include a fastening feature 210 configured to facilitate coupling the anatomical model shell pieces 204 and 206 together to form the anatomical model shell 202. The fastening feature 210 may include, for example, a hole configured to receive a screw, pin, or other fastener; a weld joint surface, a latch, and/or the like.

According to embodiments, the anatomical model shell pieces 204 and 206 may be configured such that, when they are coupled together to form the anatomical model shell 202, the shape of the anatomical model shell 202 resembles that of an anatomical structure. In embodiments, the anatomical model shell pieces 204 and 206 may be configured to represent a general shape of an anatomical structure (e.g., a shape that is approximately similar to many or most instances of that type of structure), and/or may be configured to represent a specific anatomical structure from a certain patient. The anatomical model shell pieces 204 and 206 may be designed based on CT scans of one or more subjects, ultrasound images of one or more subjects, anatomical maps of one or more patients, generated by a mapping system, and/or the like.

As shown in FIG. 2A, an electrode assembly 212 is coupled to each of a number of the apertures 208. Each electrode assembly 212 is coupled, via a wire 214, to a model control system (e.g., the model control system 108 depicted in FIG. 1A). In embodiments, an electrode assembly 212 may be coupled to each aperture 208, while, in other embodiments, electrode assembly 212 may be coupled to a set of apertures 208 such as, for example, a set 216 of apertures 208 that correspond to an activation propagation path. As shown in FIGS. 2B and 2C, the set 216 of apertures 208 that correspond to a particular activation path may be designated using a color that differs from a color associated with other apertures 208. Embodiments may include different sets 216 of apertures 208, each corresponding to a different type of activation path, and each identified using a different color or other visual feature.

Figure 2D:
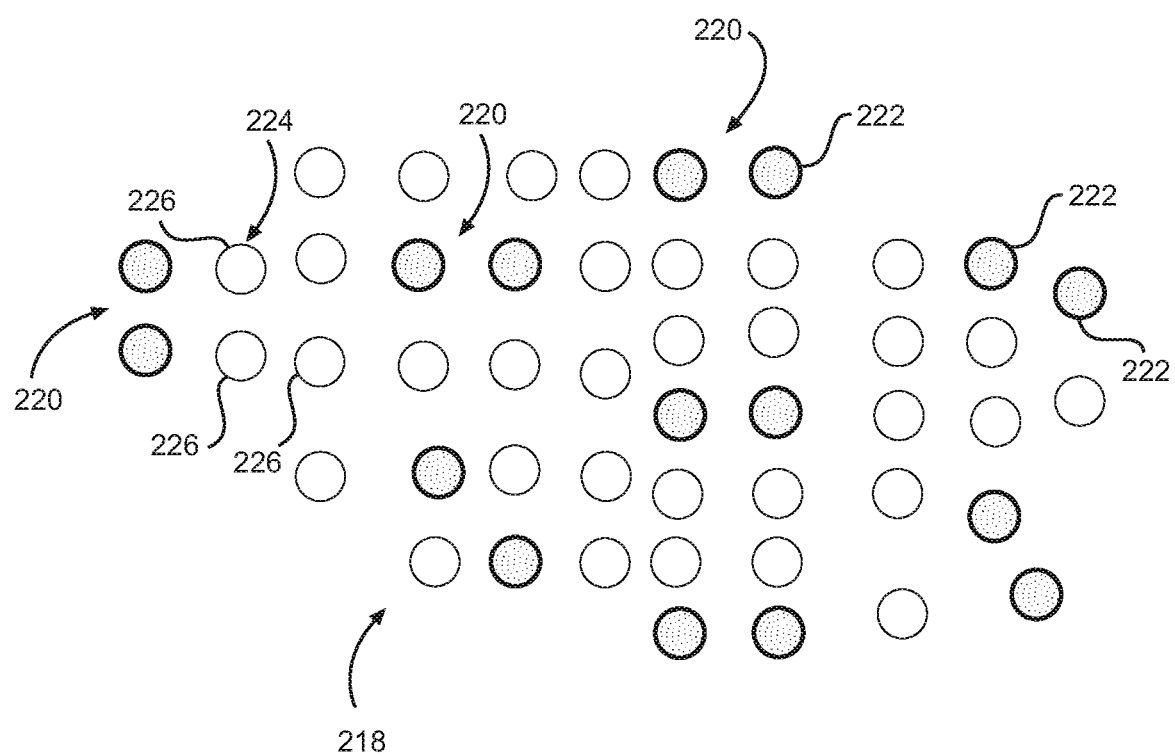
FIG. 2D depicts a portion of an illustrative electrode arrangement, in accordance with embodiments of the disclosed subject matter.

FIG. 2D depicts a portion of an illustrative electrode arrangement 218, in accordance with embodiments of the disclosed subject matter. The electrode arrangement 218 depicts an illustrative portion of a surface of a electroanatomical model having a number of pairs 220 of occupied apertures 222 (e.g., the apertures 208 depicted in FIGS. 2A-2C) to which pairs of electrode assemblies (e.g., the electrode assembly 212 depicted in FIG. 2A) are coupled. As shown, pairs 224 of empty apertures 226 (i.e., apertures to which no electrode assembly is coupled) may be disposed between adjacent pairs 220 of occupied apertures 222. In embodiments, between one and four pairs (e.g., between one and three pairs, between two and three pairs, etc.) 224 of empty apertures 226 may be disposed between each adjacent pair 220 of occupied apertures 222. In this manner, for example, electrode pairs may be approximately uniformly distributed across the surface of at least a portion of an electroanatomical model which has been found, for example, to increase the accuracy of the simulation of cardiac activation wavefront propagation. According to embodiments, any number of different arrangements, or combinations of arrangements, of occupied and empty apertures may be used.

In embodiments, the electrode assemblies 212 may be removable, while in other embodiments, the electrode assemblies 212 may be fixed. In some embodiments, one or more electrode assemblies 212 are fixed, and one or more other electrode assemblies 212 are removable. In embodiments, for example, one or more of the electrode assemblies 212 may be fixed to an aperture by forming the electrode of the electrode assembly within an aperture (e.g., by at least partially filling the aperture with a mixture that hardens to become the electrode. In embodiments, an electrode assembly 212 may be configured to be removable by configuring the electrode assembly to be removably coupled to a coupling feature of an aperture. Examples of removable coupling mechanisms include mating threads (e.g., that facilitate screwing the electrode assembly into the aperture), snap features, quarter-turn twist-lock interfaces, interference fits, and/or the like.

The illustrative anatomical model assembly 200 and illustrative electrode arrangement 218 shown in FIGS. 2A-2D is not intended to suggest any limitation as to the scope of use or functionality of embodiments of the present disclosure. Neither should the illustrative anatomical model assembly 200 be interpreted as having any dependency nor requirement related to any single component, arrangement, or combination of components and/or arrangements illustrated therein. Additionally, various components depicted in FIGS. 2A-2D may be, in embodiments, integrated with various ones of the other components and/or arrangements depicted therein (and/or components and/or arrangements not illustrated), all of which are considered to be within the ambit of the present disclosure.

Figure 3A:
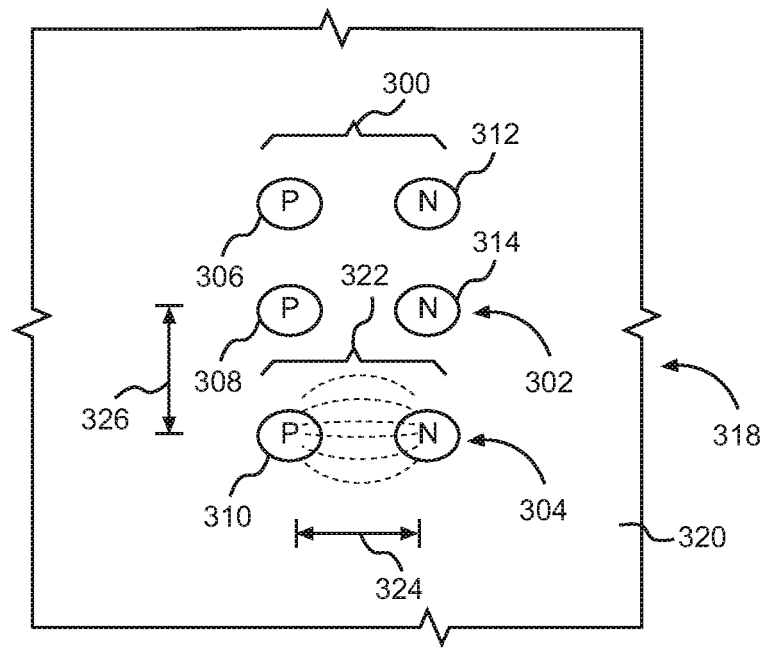
FIG. 3A is a schematic diagram depicting an array of electrodes positioned in an anatomical model shell, in accordance with embodiments of the disclosed subject matter.
Figure 3B:
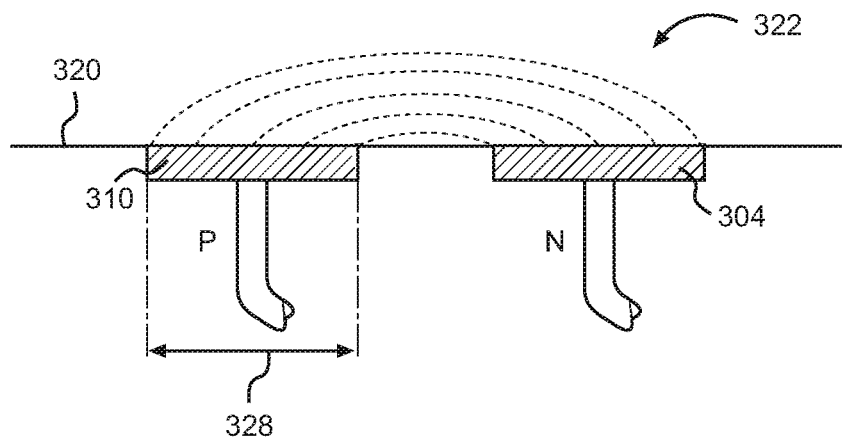
FIG. 3B is a schematic diagram depicting a pair of electrodes positioned with an anatomical model assembly, in accordance with embodiments of the disclosed subject matter.

According to embodiments, the apertures of an anatomical model shell, as described herein, are formed in pairs to facilitate using pairs of electrode assemblies for producing electrical fields that simulate electrical signals associated with the anatomical structure to which the anatomical model corresponds. FIG. 3A is a schematic diagram depicting an array of electrodes positioned in an anatomical model shell, in accordance with embodiments of the disclosed subject matter; and FIG. 3B is a schematic diagram depicting a pair of electrodes positioned with an anatomical model assembly, in accordance with embodiments of the disclosed subject matter. According to embodiments, each electrode may be included in an electrode assembly (e.g., an electrode assembly 212 depicted in FIG. 2A).

As shown in FIG. 3A, the array of electrodes includes electrode pairs 300, 302, and 304, each pair 300, 302, and 304 including a first electrode 306, 308, and 310, respectively, and a second electrode 312, 314, and 316, respectively. The first electrodes 306, 308, and 310 may be operated as positive electrodes, while the second electrodes 312, 314, and 316 may be operated as negative electrodes. In embodiments, the first electrodes 306, 308, and 310 may be operated as negative electrodes, while the second electrodes 312, 314, and 316 may be operated as positive electrodes. Any other combination of polarities may be assigned to the various electrodes 306, 308, 310, 312, 314, and 316. Each of the electrodes 306, 308, 310, 312, 314, and 316 is depicted as being coupled to an anatomical model shell 318 having an inner surface 320.

As depicted in FIGS. 3A and 3B, for example, a given pair 304 of electrodes 310 and 316 is configured to, upon being provided electrical energy, produce an electrical field 322 that may have electric field lines oriented approximately in the manner depicted in FIGS. 3A and 3B. The strength and resolution of the electric field 322 may be configured based on the electrode design, the position and/or orientation of the electrodes 310 and 316 with respect to one another, the position and/or orientation of the electrodes 310 and 316 with respect to other electrodes, the position and/or orientation of the pair 304 of electrodes 310 and 316 with respect to other pairs of electrodes, and/or the like. For example, the electrode array may be configured based on a distance 324 between the electrodes 310 and 316 of the pair 304, a distance 326 between a first pair 304 and a second pair 302, a diameter 328 of each electrode, an amount of electrical energy provided to the electrodes, and/or the like. In embodiments, for example, the electrode array may be configured to minimize the distances 324 and 326 and the amount of electrical energy provided, while ensuring that the resulting electric field 322 is able to be sensed by a mapping probe when the anatomical model assembly is disposed in a saline solution within a simulation chamber. According to embodiments, the distance 324 may be between approximately 3 mm and approximately 20 mm; the distance 326 may be between approximately 3 mm and 10 mm; and the diameter 328 may be between approximately 1 mm and 3 mm (e.g., approximately 2 mm). In embodiments, the distance 324 may be between approximately 3 mm and 1.5 cm. For example, through experimentation, the inventors have found that an electrode-to-electrode distance (e.g., the distance 324) of 1 cm with a driving voltage of 0.1 volts (V) was sufficient for generating electrical signals that are able to be mapped throughout the entire model. In embodiments, the length of the wires that power the electrodes may be increased, in which case the voltage may be increased. In embodiments, for example, the driving voltage for the electrodes may be between approximately 0.05V and 1V (e.g., between approximately 0.1V and 0.5V).

According to embodiments, electrode design may be configured to facilitate an optimization of the considerations described above with respect to electrode position and orientation, electrical energy, and resulting field strength. To achieve this, the electrodes are configured to be have relatively high capacitance to facilitate conduction through the saline solution to produce an electric field with enough strength that it can be sensed using a mapping probe. This may be achieved via the electrode material, the configuration, and/or the like. That is, for example, an electrode with a relatively large surface area may facilitate minimizing the distances 324 and 326, the diameter 328, and the driving voltage, as described above.

According to embodiments, each electrode may be formed using at least one of carbon black and silver epoxy. For example, in embodiments, each electrode may be formed using a mixture of approximately 50% carbon black and approximately 50% silver epoxy. In embodiments, each electrode may be formed using a combination of between approximately 5% and approximately 95% of silver epoxy by volume and between approximately 5% and approximately 95% carbon black by volume. The combination of these materials provides a stable mixture that does not dissolve quickly during use. Additionally, carbon black has a large surface area per particle, which facilitates increasing the capacitance of the electrode. In experiments using platinum wire for driving the electrodes, the mixture of approximately 50% carbon black and approximately 50% silver epoxy was found to produce a measurable electrical field with a driving voltage of approximately 0.1 volts (V).

According to embodiments, any number of different materials may be used to form the materials. For example, organic materials may be used, including, but not limited to, carbon composite based materials such as, for example, conductive blacks, conductive carbon fibers, polymeric binders as composites, and/or the like. For example, high-capacitance material composites may include mixtures of polymeric binders, conductive blacks, carbon fibers, metallic particles, oxides of metallic particles, and/or the like. According to embodiments, any material with enough surface area and capacitance to be capable of generating fields required to achieve functionality described herein may be used. For example, high surface area materials may include pure metals and/or conductive oxides of metals such as, for example, platinum, iridium, palladium, silver, gold, and/or the like. In embodiments, these may be deposited, stabilized, and/or bonded in any number of different ways such as, for example, vapor deposition, thermal decomposition, reduction, and/or the like. In embodiments, these may be adhered to a substrate using any number of different adhesives. Any number of different combinations of the above may also be used in embodiments.

Additionally, the arrangement of electrodes in an array may be configured to result in production of realistic images of the simulated surfaces. For example, in embodiments, an anatomical model of a human atrium having 84 pairs of electrodes may be configured to generate, via a mapping system, a map that appears realistic.

Each of the plurality of electrodes may have an approximately cylindrical shape and may have a diameter of between approximately one millimeter (mm) and approximately 10 mm. In embodiments, each electrode may have a diameter of approximately 2 mm. In embodiments, the electrodes may be configured according to any number of other shapes, diameters, and/or the like. Additionally, the electrodes may be positioned within the apertures in any number of various configurations. For example, the distance between adjacent electrodes of an electrode pair may be between approximately 1 mm and approximately 10 mm. The close spacing of the electrodes helps retain the electrical field/current flow between the two electrodes of each pair to be local, therefore facilitating a useful spatial resolution of the model. The high capacitance of the electrode material facilitates the signal pickup by the mapping catheter, thus enables a useful signal sensitivity of the model.

Figure 4A:
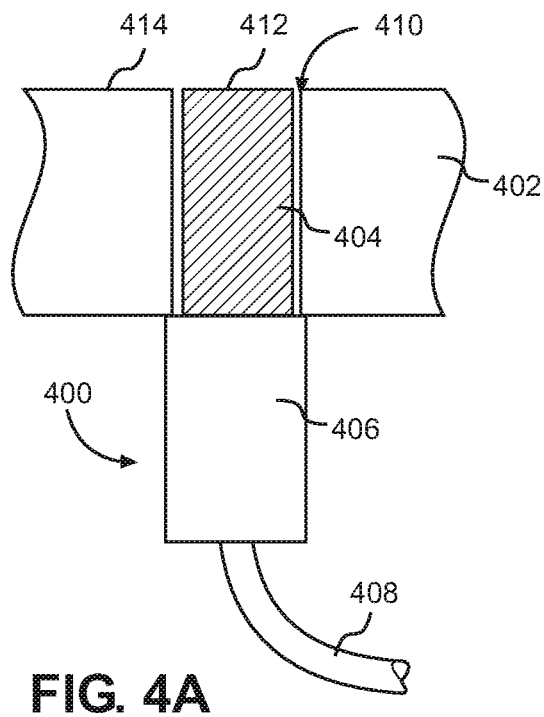
FIGS. 4A-4C are schematic diagrams depicting an illustrative electrode assembly positioned with an anatomical model shell, in accordance with embodiments of the disclosed subject matter.
Figure 4B:
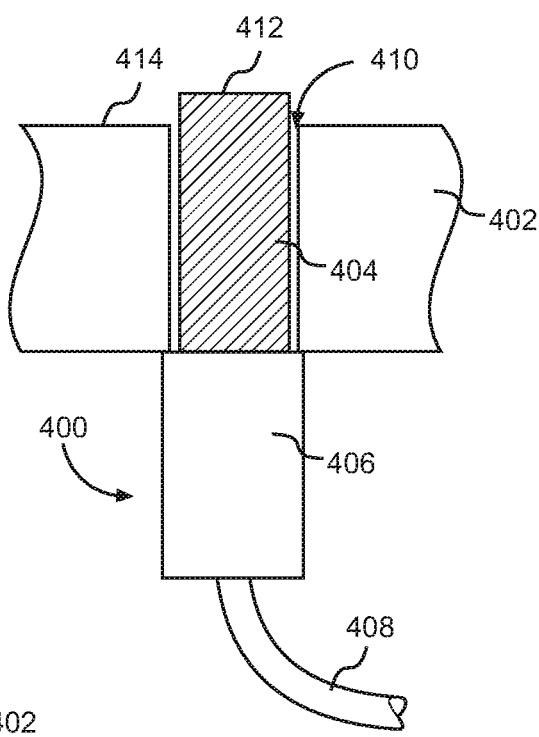
Figure 4C:
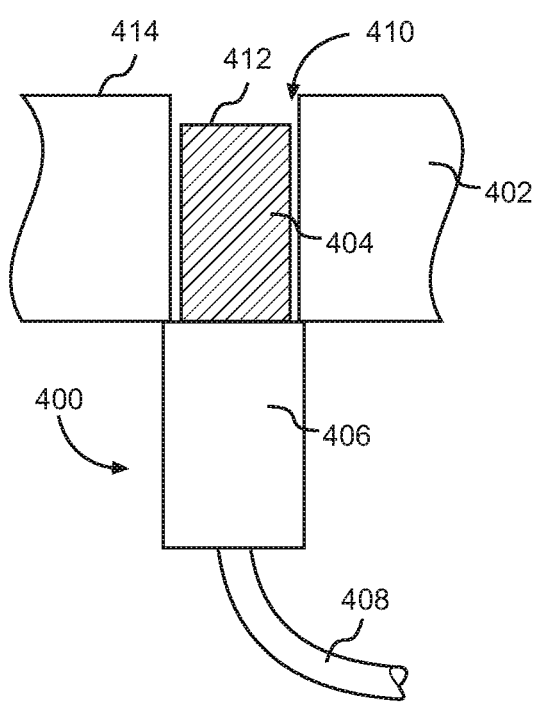

FIGS. 4A-4C are schematic diagrams depicting an illustrative electrode assembly 400 positioned with an anatomical model shell 402, in accordance with embodiments of the disclosed subject matter. The electrode assembly 400 may be, be similar to, include similar features as, include, or be included within the electrode assemblies 212 depicted in FIG. 2A, and/or the electrodes 306, 308, 310, 312, 314, and 316 depicted in FIGS. 3A and 3B.

As shown, the electrode assembly 400 includes an electrode 404 coupled to a header 406, which is configured to receive a wire 408 that provides electrical energy to the electrode 404. The electrode 404 is configured to be at least partially disposed within an aperture 410 defined in the anatomical model shell 402. As shown in FIG. 4A, the electrode 404 may be configured to be disposed within the aperture 410 such that an end surface 412 (e.g., a surface that faces the interior of the anatomical shell 402) is approximately flush with an inside surface 414 of the anatomical shell 402. In embodiments, as shown in FIG. 4B, the electrode 404 may be configured to be disposed within the aperture 410 such that the end surface 412 protrudes with respect to the inside surface 414 of the anatomical shell. In embodiments, as shown in FIG. 4C, the electrode 404 may be configured to be disposed within the aperture 410 such that the end surface 412 is recessed with respect to the inside surface 414 of the anatomical shell. Any of the configurations depicted in FIGS. 4A-4C may be, in embodiments, sufficient to facilitate production of an electric field that can be sensed by a mapping probe. The configurations depicted in FIGS. 4A and 4C may facilitate minimizing (or eliminating) contact between the mapping probe and the electrode 404.

The illustrative electrode assemblies and configurations shown in FIGS. 3A, 3B, and 4A-4C are not intended to suggest any limitation as to the scope of use or functionality of embodiments of the present disclosure. Neither should the illustrative electrode assemblies and configurations be interpreted as having any dependency nor requirement related to any single component or combination of components illustrated therein. Additionally, various components depicted in FIGS. 3A, 3B, and 4A-4C may be, in embodiments, integrated with various ones of the other components and/or configurations depicted therein (and/or components and/or configurations not illustrated), all of which are considered to be within the ambit of the present disclosure.

Figure 5:
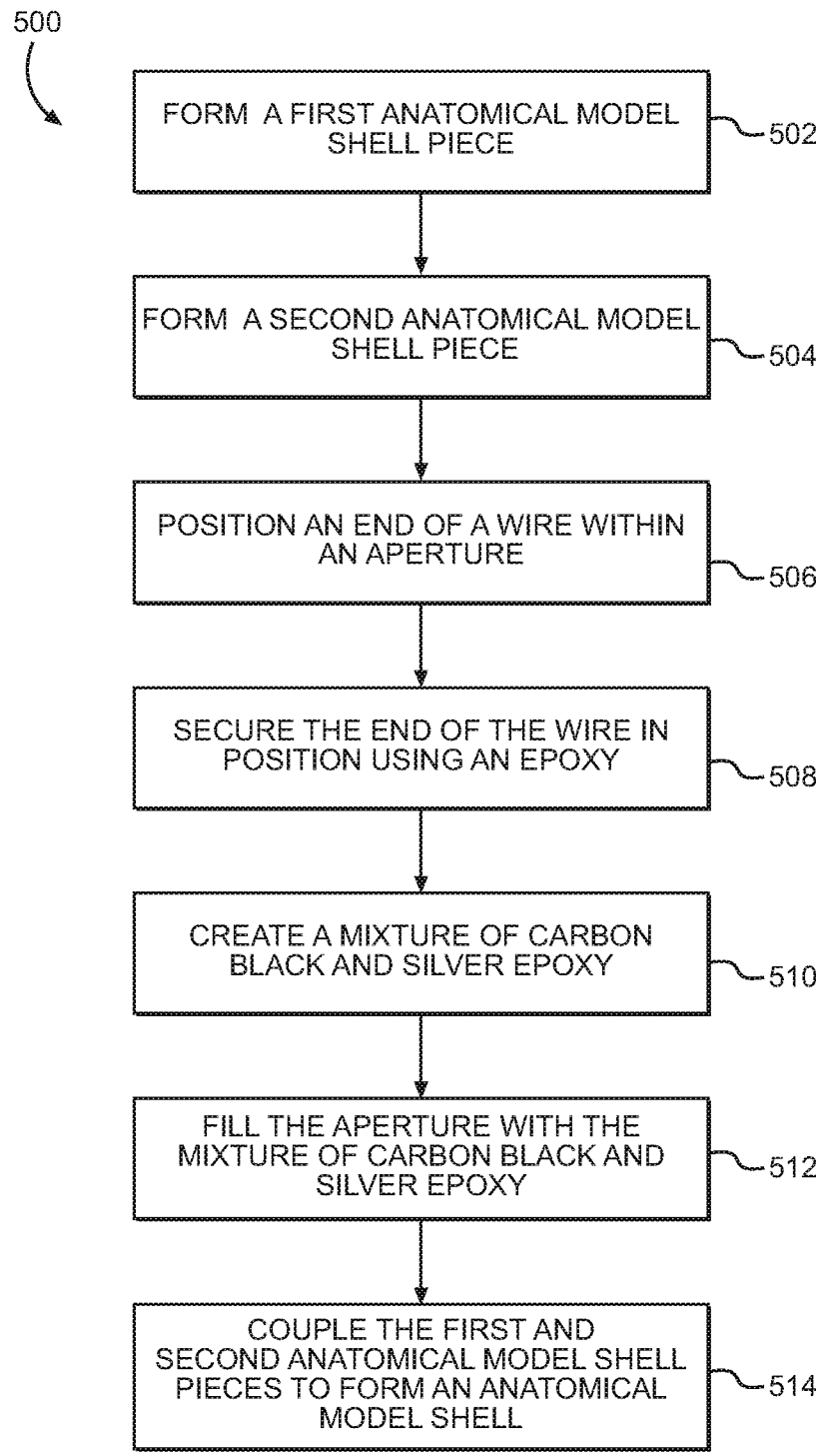
FIG. 5 is a flow diagram depicting an illustrative method of producing an anatomical model simulator system, in accordance with embodiments of the disclosed subject matter.

Embodiments include, as explained above, a system for simulating an anatomical structure, in accordance with embodiments of the disclosed subject matter. FIG. 5 is a flow diagram depicting an illustrative method 500 of producing an anatomical model simulator system (e.g., the system 102 depicted in FIGS. 1A & 1B). According to embodiments, the method 500 includes forming a first anatomical model shell piece (block 502); and forming a second anatomical model shell piece (block 504). The first anatomical model shell piece may be formed having a first group of apertures defined therein. In embodiments, the first and second anatomical shell pieces may be formed solid, in which case apertures may be formed by punching them out, drilling them, and/or the like.

Embodiments of the method 500 further include positioning an end of a wire within an aperture (block 506), and securing the end of the wire in position using an epoxy (block 508). As shown in FIG. 5, the method 500 further includes creating a mixture of carbon black and silver epoxy (block 510), filling the aperture with the mixture of carbon black and silver epoxy (block 512); and coupling the first and second anatomical model shell pieces to form an anatomical model shell (block 514).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An anatomical model simulator system, comprising:
    a physical anatomical model assembly configured to represent an anatomical structure, comprising:
        an anatomical model shell having a plurality of apertures defined therein; and
        a plurality of electrodes, wherein each electrode of the plurality of electrodes is disposed within one of the plurality of apertures, and wherein each electrode comprises at least one of carbon black and silver epoxy; and
    a model control system, comprising:
        a power supply configured to deliver electrical energy to the plurality of electrodes; and
        a controller configured to control the delivery of the electrical energy to the plurality of electrodes to simulate in the physical anatomical model electrical activity of the anatomical structure.

2. The anatomical model simulator system of claim 1, the anatomical shell comprising an inside surface, wherein an end surface of each electrode of the plurality of electrodes is recessed with respect to the inside surface of the anatomical shell.

3. The anatomical model stimulator system of claim 1, wherein the anatomical shell is formed from a three-dimensionally printed polymer.

4. The anatomical model stimulator system of claim 1, the plurality of electrodes comprising a plurality of pairs of electrodes, each of the plurality of pairs of electrodes comprising a positive electrode and a negative electrode.

5. The anatomical model stimulator system of claim 4, wherein each of the plurality of pairs of electrodes is configured to generate an electric field having a magnitude that can be sensed by a mapping probe.

6. The anatomical model stimulator system of claim 5, wherein the electrode is configured to be driven with approximately 0.1 volts.

7. The anatomical model stimulator system of claim 1, the controller comprising:
    a switch circuit configured to selectively activate each of the plurality of electrodes;
    a memory comprising a program component, the program component comprising computer-executable instructions; and
    a processor configured to access the program component via the memory and to executed the computer-executable instructions, wherein the computer-executable instructions are configured to cause the processor to control the power supply.

8. The anatomical model stimulator system of claim 7, wherein the controller is configured to cause the power supply to deliver the electrical energy according to an arrhythmia pattern to cause the plurality of electrodes to simulate a propagating cardiac electrical signal corresponding to an arrhythmia.

9. The anatomical model stimulator system of claim 8, wherein the controller is configured to prevent electrical energy from being delivered to one or more pairs of electrodes to simulate scar tissue.

10. The anatomical model stimulator system of claim 1, each of the plurality of electrodes comprising a mixture comprising approximately 50% carbon black and approximately 50% silver epoxy.

11. The anatomical model stimulator system of claim 10, each of the plurality of electrodes having an approximately cylindrical shape.

12. The anatomical model stimulator system of claim 10, wherein each of the plurality of electrodes comprises a diameter of approximately two millimeters.

* * * * *